(12) United States Patent
Familant

(10) Patent No.: US 8,676,605 B2
(45) Date of Patent: Mar. 18, 2014

(54) DELPHI METHOD FOR MEDICAL CODING

(75) Inventor: Mark Elliott Familant, Tinton Falls, NJ (US)

(73) Assignee: Artificial Medical Intelligence, Inc., Eatontown, NJ (US)

( * ) Notice: Subject to any disclaimer, the term of this patent is extended or adjusted under 35 U.S.C. 154(b) by 438 days.

(21) Appl. No.: 12/519,899

(22) PCT Filed: Dec. 20, 2007

(86) PCT No.: PCT/US2007/026094
§ 371 (c)(1),
(2), (4) Date: Oct. 20, 2009

(87) PCT Pub. No.: WO2008/079305
PCT Pub. Date: Jul. 3, 2008

(65) Prior Publication Data
US 2010/0036680 A1  Feb. 11, 2010

Related U.S. Application Data

(60) Provisional application No. 60/876,056, filed on Dec. 20, 2006, provisional application No. 60/919,076, filed on Mar. 20, 2007.

(51) Int. Cl.
*G06Q 50/00* (2012.01)

(52) U.S. Cl.
USPC .................................................. 705/3; 705/2

(58) Field of Classification Search
USPC .......................................................... 705/2–3
See application file for complete search history.

(56) References Cited

U.S. PATENT DOCUMENTS

| 7,249,040 B1 * | 7/2007 | Binns et al. ........................ 705/4 |
| 2005/0192792 A1 | 9/2005 | Carus et al. |
| 2005/0240439 A1 | 10/2005 | Covit et al. |
| 2006/0252479 A1 | 11/2006 | Lydon et al. |

OTHER PUBLICATIONS

International Search Report, PCT/US07/26094, Date: May 7, 2008.

* cited by examiner

*Primary Examiner* — Sind Phongsvirajati
(74) *Attorney, Agent, or Firm* — Lerner, David, Littenberg, Krumholz & Mentlik, LLP

(57) ABSTRACT

Systems and methods provide confirmation of accuracy of determining medical codes for medical records. The technology may include processor control instructions or steps for establishing a collection of medical documents as a test sample and for determining a convergence of assigned medical codes for the sample that have been assigned by a plurality of coders to establish a standard of one or more accepted medical codes for the sample. The technology may include instructions for applying the sample to a coding system to obtain a determined medical code for the sample; and for comparing the determined code to the accepted medical codes to rate the coding system's accuracy. In some embodiments, the determining a convergence of determined medical codes may be obtained by a software coding algorithm that automatically assigns medical codes to medical records. Moreover, the comparing step may be performed by an algorithm that automatically calculates a rate of the coding system.

14 Claims, 5 Drawing Sheets

ROUND ONE INTERFACE

ROUND TWO INTERFACE

DELPHI METHOD FOR MEDICAL CODING

CROSS-REFERENCES TO RELATED APPLICATIONS

This application claims the benefit of the filing date of U.S. Provisional Patent Application No. 60/876,056 filed Dec. 20, 2006 and U.S. Provisional Patent Application No. 60/919,076 filed Mar. 20, 2007, the disclosures of which are hereby incorporated herein by reference.

BACKGROUND

Applying medical codes to documentation generated in a hospital or physician's office requires trained practitioners to apply a complicated set of rules to determine which of the thousands of ICD9 and CPT codes apply to any given patient during a particular encounter. Although medical coders are trained and certified to perform this function, there is a great deal of variance between coders in how they perform this task (Department of Veteran Affairs, 1993; Morris, Heinze, Warner, et al., 2000; Morsch, Heinze, & Byrd, 2004).

Coder variability has an obvious impact on the quality of hospital coding. Beyond this, coder variability makes it difficult to establish a standard by which coders and computer assisted coding systems (CACs) can be evaluated. This need for a "gold standard" is now an acknowledged need in the coding industry (Morris, Heinze, Warner, et al., 2000; Resnik, Nossal, Schnitzer et al., 2006). Because such a standard will necessarily be based on human judgment, a process needs to be created by which the variant products of human coders can be transformed into a consensus view for any given set of medical documentation. That is, there needs to be a process by which coders who may initially disagree on which codes should be applied to a given set of documents, can come to an agreed upon consensus on how these documents should be coded. Artificial Medical Intelligence (AMI) has developed, EMscribe GS, a consensus building process for this purpose by adapting some of the techniques used in the Delphi Method to the medical coding problem.

One of the broader definitions of the Delphi Method is as follows:

"Delphi may be characterized as a method for structuring a group communication process so that the process is effective in allowing a group of individuals, as a whole, to deal with a complex problem." (Linstone & Turoff, 2002).

The defining characteristics of the Delphi method include:
Receiving input from a variety of experts about a topic of interest, typically anonymously.
Obtaining this input in a structured way (e.g. a questionnaire, an opinion on a defined problem, a set of rating scales).
Evaluation of the input by using a set of criteria, and filtering and summarizing it if necessary.
Presenting this evaluation to the experts again and giving them an opportunity to comment on it and change their input based on the evaluation.
Evaluating this second round of input and representing this second evaluation to the experts.
Iteratively repeating the process until the opinions of the experts are stable and, in some instances, have converged on a consensus opinion (Linstone & Turoff, 2002).

Since its development in the 1950s at the RAND corporation, the Delphi method has been used for a wide range of applications including:

1. Development of policy related to resource management and drug abuse
2. Project estimation
3. Risk analysis
4. Technology projections and
5. Trend analysis (Linestone & Turoff, 2002).

To date it has not been used for the more structured task of medical coding.

SUMMARY

An example of the present technology includes methods for confirming accuracy of coders. The method may include establishing a collection of medical documents as a test sample; determining a convergence of assigned medical codes for the test sample that have been assigned by a plurality of coders to establish a standard of one or more accepted medical codes for the test sample; applying the test sample to a coding system to obtain one or more determined medical codes for the test sample; and comparing the determined codes to the accepted medical codes to rate the accuracy of the coding system. In some embodiments, the determined medical codes may be obtained by a software coding algorithm that automatically assigns medical codes to medical records. Moreover, the comparing step may be performed by a software algorithm that automatically calculates a rate of the coding system.

In some embodiments, the plurality of coders may include at least one automated coding system. Moreover, the determined medical codes may be obtained from human coders through a computer system that accepts data medical codes assigned with a user interface of the computer system. In addition, the plurality of coders may optionally include at least one or more automated coding system(s) that accepts data medical codes assigned with a user interface of the coding system. In another embodiment of the technology, the plurality of coders includes at least one automated coding system that includes a software algorithm that automatically assigns medical codes to the collection of medical records.

In other embodiments of the technology, a method for coding medical documents may include presenting a set of documents to each of a plurality of game contestants in a user interface. The method may further include receiving input from at least one of the user interfaces concerning a potential classification code for the set of documents. A score may then be determined for at least one of the plurality of game contestants based on the received input from the user interface. In one embodiment, the method may further involve determining an accepted set of classification codes for the set of documents from input of the user interfaces of the plurality of game contestants. Moreover, the method may also include determining the score based on the determination of the accepted classification codes.

At least one embodiment of the technology involves an automated system for confirming accuracy of coders. The system may include processor control instructions to establish a collection of electronic medical documents as a test sample and processor control instructions to determine in a computer processor a convergence of assigned medical codes for the test sample that have been assigned by a plurality of coders to establish a standard of one or more accepted medical codes for the test sample. The system may further include processor control instructions to apply the test sample to a coding system to obtain one or more determined medical codes for the test sample and processor control instructions to compare in a computer processor the determined codes to the accepted medical codes to rate the accuracy of the coding system. In an embodiment, the determined medical codes may be obtained by a software coding algorithm that automatically assigns medical codes to medical records. In another embodiment, the comparing is performed by a software algorithm that automatically calculates a rate of the coding system.

In another embodiment, the plurality of coders of the system may include at least one automated coding system. Moreover, the determined medical codes may be obtained by a computer system that accepts data medical codes assigned with a user interface of the computer system. Furthermore, the plurality of coders may include at least one or all automated coding systems that accept data medical codes assigned with a user interface of the coding system. In a still further embodiment, the plurality of coders may include at least one automated coding system that includes a software algorithm that automatically assigns medical codes to the collection of medical records.

In another embodiment of the technology, an automated system for coding medical documents may include user interfaces to present a set of electronic medical documents to each of a plurality of game contestants. The system may further include processor control instructions programmed to receive input from at least one of the user interfaces concerning a potential classification code for the set of electronic medical documents, and processor control instructions to determine a score for at least one of the plurality of game contestants based on the received input from the user interface. In an embodiment, the automated system may also include processor control instructions to determine an accepted classification code for the set of electronic medical documents from input of the user interfaces of the plurality of game contestants. Moreover, the automated system may further include processor control instructions to determine the score based on the determination of the accepted classification code.

Additional aspects of the technology will be apparent from a review of the following description and drawings.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Figure 1:
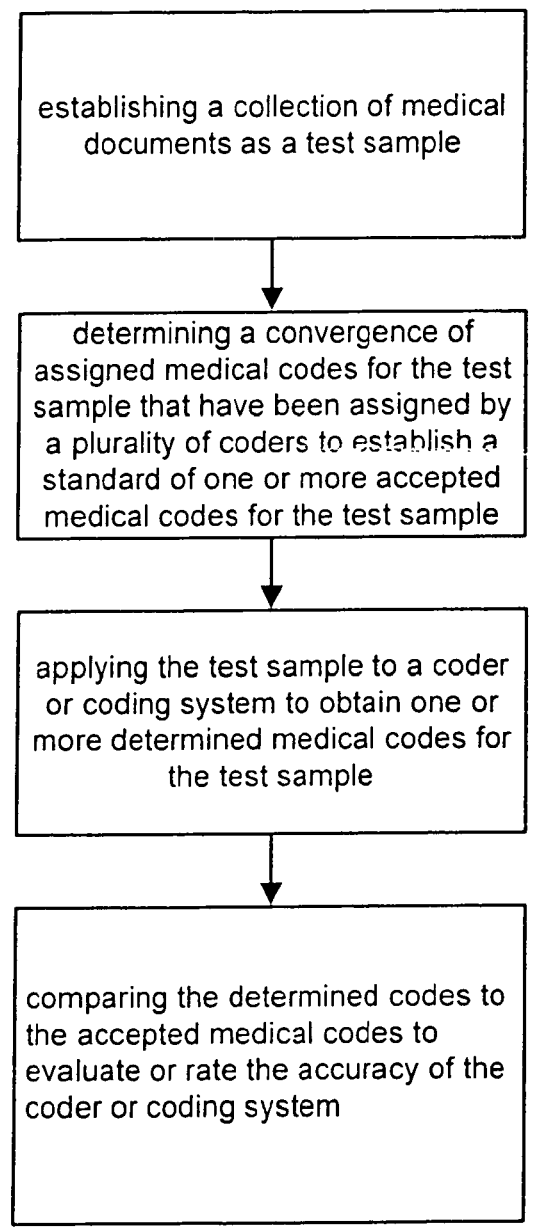
FIG. 1 is a block diagram of an example embodiment of a method of assigning medical codes of the present technology.

We have observed that the task of medical coding exhibits characteristics that we believe make it a candidate for the Delphi approach including the following attributes: include:
1. Medical coding is a complicated task
2. There is a lack of a generally agreed upon "solution" (set of codes) that could be applied to any set of documents.

Applying the Delphi Method to the general day to day task of coding medical documents would be too expensive to implement. However, we have applied it for the more occasional task of creating a "gold standard" by which an organization could evaluate coders or computer assisted coding solutions. AMI's Delphi Method Of Medical Coding (DMMC) incorporated in EMscribe GS is designed to do just these types of tasks.

The Delphi Method Of Medical Coding (DMMC) utilized in EMscribe GS is based on the premise that collective expertise of a group of experienced coders will result in more accurately coded documentation than (for the most part) the application of that expertise by any individual coder. Coders will correct errors made by others in the group, they will think of things that may escape the attention of any individual coder, they will check each others work, etc. As a result, the consensus view will be more accurate and more complete than the product of any individual coder's efforts.

One approach using the DMCC process employed by EMscribe GS is illustrated by the following methodology, which may be implemented through the use of automated or computerized systems in the performance of the methodology (in whole or in part) depending on the nature of the particular characteristics as discussed below:

1. A test set of medical documentation is assembled.
2. Coders are recruited.
3. Coders are presented with individual items from the test set and they then apply codes to these items. These codes are then referred to as the Round One results.
4. The Round One results are then analyzed. Codes for which agreement has been reached at a level above some criterion level are identified. Other codes are presented to the coders for a second round of evaluation.
5. Coders then examine the codes for which there is no consensus. Written statements justifying their application to the documentation or arguments why they shouldn't be applied to the documentation are generated by the coders.
6. These statements are reviewed by the coders and then for each nonconsensual code, they decide either to apply the code to the medical documentation or not. The results of this voting are referred to as the Round Two results.
7. The Round Two results are analyzed as in step 4 above, the codes for which agreement has been reached at a level above the criterion level are identified. Other codes for which there is not a sufficient level of agreement are presented to the coders for a subsequent third round of evaluation.
8. Steps five through seven are repeated until changes between rounds falls below an agreed upon level.
9. At the end of the process, codes for which no consensus is reached are arbitrarily chosen to be assigned or not assigned to the documentation based on a random selection criterion. The resulting set of codes is referred to as the consensus view for the associated set of medical documentation.

In the following sections, example steps of such a methodology are described in more detail.

Assembling Medical Documentation for a Test Set

The composition of a test set preferably depends on the evaluation goals of the gold standard and the domain of interest. Medical coding is applied to a variety of medical documents including H&P reports, consultation notes, procedure notes, in-office physician notes, and discharge summaries. The documents assembled for the test set should reflect the types of documents typically encountered by the coders who will construct the standard and who will be evaluated once the standard is constructed.

Two typical ways to characterize medical documents are by the type of medical encounter and by the patient's diagnosis. Documents can also be characterized by the kind of person generating them, the completeness of the documentation, demographic patient information, etc.

Once a set of relevant characteristics for the medical documents have been identified, each combination of characteristics that can occur should be listed (e.g. documents generated during an initial encounter for patients exhibiting symptoms of an acute myocardial infarction, documents generated during a subsequent encounter for patients diagnosed with diabetes, etc.). Each of these combinations constitutes a sampling cell.

Documents are collected that fit the characteristics of each cell. The number of documents collected for each cell depends on the variability of the documents within the cell (greater variability necessitates a larger cell sample). Beyond this, sampling can be done in two ways:
1. Sampling can be exhaustive. Under this scheme, documents are collected for every single cell. The set then becomes a comprehensive evaluation of documents that fit some defined set of criteria.
2. Sampling can be representative. Under this scheme, documents are collected in proportions reflective of the population from which the sample is derived. For example, if 10 percent of the patients in a particular setting are cardiac patients, 10 percent of the documents in the test set are from cardiac patients.

Recruiting Coders

The coders participating in the DMMC should have experience with the types of documents and types of medical coding for which the standard is being created. Beyond establishing a set of criteria which define the minimum qualifications for a participating coder, little else needs to be done. Restricting participation to only the "best" coders in an organization (as say identified by a supervisor) may not be advisable since the ability to cooperate and achieve a common understanding of how to code a document is at least as important in this task as knowledge of coding.

Presentation of Individual Test Items

Round One

An important characteristic of any Delphi method is that the identity of experts remains hidden from other experts (although it is known to the moderator). A convenient way to hide the identity of the experts but to still allow them to be distinguished within the Delphi environment is to assign each coder a "handle" or nickname. Each coder's input during Round One is tagged with the coder's handle. Coder's comments on the input are also tagged.

Coders provide their input using a standardized form (either electronic or paper). Coders should provide this input isolated from others who may be also participating in the DMMC. When coders are finished providing input, it is submitted to the moderator.

Analyzing Round One Results

The main task during this step is to identify those codes for which there is sufficient convergence of opinion so that they can be eliminated from further consideration. To do this, a criterion needs to be established. This can be set as a percentage of agreement among testers (e.g., 90% of the coders agree that code X should be applied to the chart). The remaining codes are resubmitted to the coders for round two.

Reevaluating Codes for which there is No Consensus

Round Two

Round Two consists of two stages. During the first stage, experts reexamine the codes for which there was no consensus. For each of these codes, they can either write statements in support of or against applying the code to the associated set of documentation. The comments are read and responded to by all the participating experts. After a designated period of time, comments are suspended and the second stage of Round Two occurs when the experts revote on each code for which there is no consensus.

Analyzing Round Two Results

Analysis at this step is the same as it was during Round One. The same criterion is used to define a converged opinion on whether a code should be coded or not.

Additional Rounds

Progress towards convergence can be measured by using a change score, C, defined as the ratio of the total number of codes for which convergence has been reached during the current round over the total number of codes considered before the round began. For example, if there were 10 codes for which there was no convergence prior to the beginning of the round and four codes for which there was convergence at the end of the round, the change score would be 4/10 or 0.4. Rounds are continued until the change score falls below a certain criterion amount.

Assignment of the Remaining Codes

Once the change score has fallen below criterion, decision of whether or not to assign the remaining codes is determined by a random process. This can be done using an unbiased random number generator associated with a rule governed process (e.g. odd numbers mean assign and even numbers mean don't assign).

Use of Software Tools to Facilitate DMMC

Although use of a computer system is not necessary to implement DMMC, using at least a software tool like, for example, EMscribe GS has a number of advantages including:
1. Organizing the presentation of the test set information. A chart or document can be presented electronically to experts. Experts can easily page between different parts of the documentation if there are multiple documents in this scheme.
2. Coding is integrated with the documentation presentation. Experts can assign codes to the documentation in an integrated environment that allows the coder's responses to be easily associated with the relevant documentation.
3. Scoring is automated. A computer system may then be implemented to compute which codes have a sufficient level of convergence and then can package the remaining codes so that they can be represented in future rounds.
4. Managing expert discussions around codes during individual rounds. A system can be implemented to receive, store and organize statements about codes using discussion threads similar to what is found on internet discussion boards.
5. Managing the voting on codes during rounds. A computer system may then be implemented to automatically tabulate votes and determine through this voting process whether a convergence of opinion has been formed around each code.

Artificial Medical Intelligence has designed EMscribe GS to implement aspects of these features.

DMMC Outputs

DMMC produces two outputs that can be used for evaluation purposes:

Medical Record Test Set
If done repeatedly, this process will generate a corpus of accurately coded medical records. These medical records can then be used to evaluate coders. To evaluate these new coders, they are simply asked to code the documents for which consensus coding has been obtained. Then the degree of correspondence between these coders and the consensus view can be compared. A score measuring the accuracy of these coders can be obtained employing the commonly used industry metrics of recall and precision. Appendix one includes an explanation of these two metrics.

Coder Evaluation Test
The process can also be used to evaluate the coders taking part in the DMMC process. Coders are evaluated based on their initial round of coding relative to the eventual consensus view. That is, for each coder participating it is possible to ask, what percentage of codes generated during the initial round were also codes that appeared in the consensus view and how much overcoding did each coder do relative to the consensus view. Recall and precision statistics can be generated for these coders in the same manner as above.

For example, in an embodiment of such a method as illustrated in FIG. 1, that may be implemented as a system, such as with software of a computer system, for confirming accuracy of coders (either people and/or automated coding systems such as an automated coding system described in U.S. patent application Ser. No. 11/106,817, filed on Apr. 15, 2005, the entire disclosure of which is incorporated herein by reference), the method may include one or more of the following: establishing a collection of medical documents as a test sample; determining a convergence of assigned medical codes for the test sample that have been assigned by a plurality of coders to establish a standard of one or more accepted medical codes for the test sample; applying the test sample to a coder or coding system to obtain one or more determined medical codes for the test sample; comparing the determined codes to the accepted medical codes to evaluate or rate the accuracy of the coder or coding system.

Another embodiment of the technology may be implemented with an application of game techniques for medical coding. In addition to the need for a gold standard, there is a need within the medical coding community to provide a quantitative and objective means for evaluating medical coders. Such a measurement instrument could be used by hospitals and other institutions that hire medical coders to evaluate potential candidates for medical coding positions and determine compensation for existing medical coding staff. Artificial Medical Intelligence (AMI) has developed, the Coding Game, an online game for the medical coding community that produces both a medical coding Gold Standard and a quantitative evaluation for any medical coder who plays the game.

Applying the Delphi Method to the typical daily task of coding medical documents could be too expensive. However, implementing the Delphi Method as an interactive game in which Medical Coders could compete, potentially win prizes and receive a ranking provides significant incentives to the participants, to the extent that coders are likely to participate for free and may even pay a subscription fee in order to be able to play.

The Coding Game as an Instance of Human Computation

Human based computation is a technique whereby a computational process is performed partially by a computer and partially by one or more humans. In human computation, a problem is presented to multiple individuals to solve. A computer then collects, interprets and integrates the information provided by these individuals to produce a solution (Wikipedia, 2007). The use of gaming techniques to provide incentives for individuals to participate in human computation activities has been used in other contexts such as labeling pictures (von Ahn, 2003) and collecting common-sense facts (von Ahn, 2006). By taking the standard Delphi technique described above and modifying it, Medical Coding can be transformed into a competitive game that will produce both a gold standard for medical records and a quantitative score for each participant in the game, a score that represents that individual's coding ability.

Implementing the Coding Game

Methodology

The coding game is played using a database of de-identified and/or fictitious medical records. A medical record consists of a series of documents that would be generated by medical personnel during any patient encounter. Examples of documents in a medical record include the History and Physical, Operative Report, Consultation Note, Discharge Summary, etc.

A key aspect of the game is the method used to determine if the assignment of a given code assigned to a medical record or document is valid or not. The Coding Game adopts a standard derived from the DMMC cited earlier. The assignment of a medical code to a medical document or medical record will be considered valid if a certain predetermined percentage of participants (called the criterion percentage), coding the same document or record, assign the same code. For example, given an 80% criterion percentage, if 80% or more of the coders evaluating a given medical document determine that a certain code should be appropriately assigned to that document that code would be considered a valid assignment. Codes meeting this criterion will be known as consensus codes.

For the purposes of implementing the Coding Game, both the medical records and their individual component documents grouped into cases are classified into three categories:
1. Medical Records Or Documents For Which Complete Consensus Has Been Obtained. These records are associated with consensus codes and only consensus codes. Records falling into this category will be known as Complete Consensus Records (CCRs).
2. Medical Records Or Documents For Which Incomplete Consensus Has Been Obtained. These are records are associated with medical codes, at least some of which, are not consensus codes. Records falling into this category will be known as Incomplete Consensus Records (ICRs).
3. Medical Records Or Documents That Are Not Yet Associated With Medical Codes. These are medical records that have not yet been coded. Records falling into this category will be known as Uncoded Records (URs).

Figure 2:
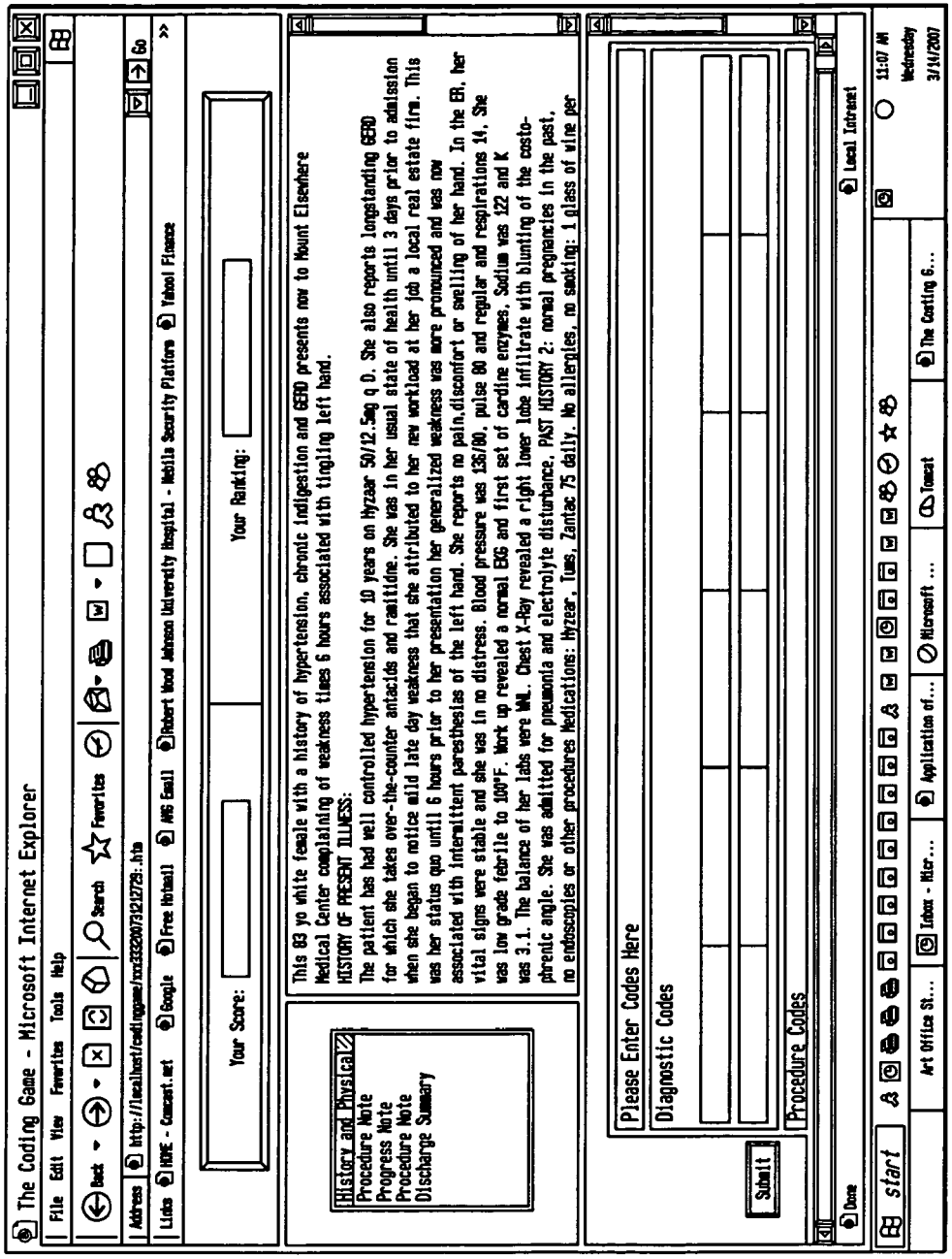
FIG. 2 shows an embodiment of a user interface display when assigning codes during a gaming embodiment of the present technology.
Figure 3:
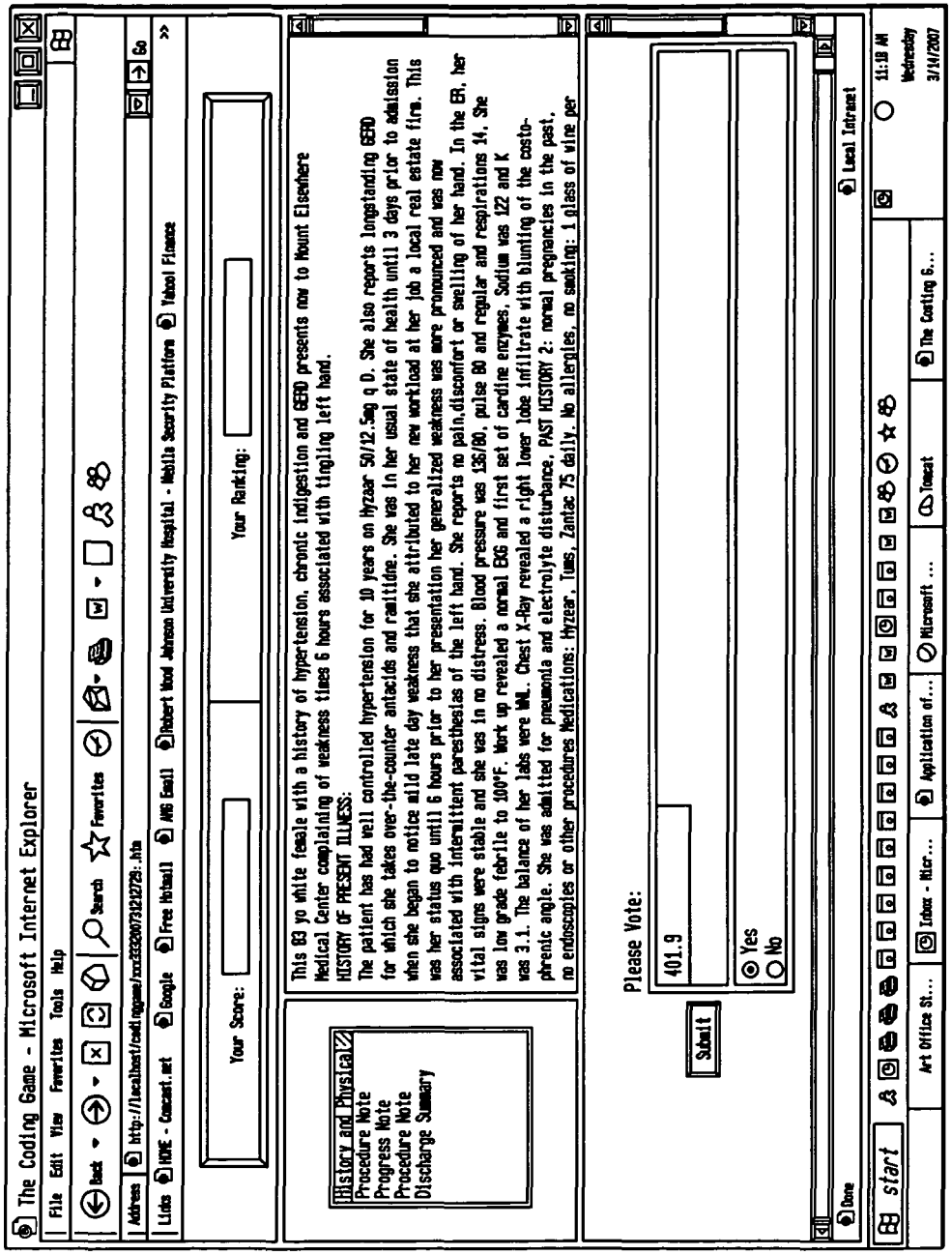
FIG. 3 illustrates an embodiment of a generic user interface display when voting for codes during a gaming embodiment of the present technology.
Figure 4:
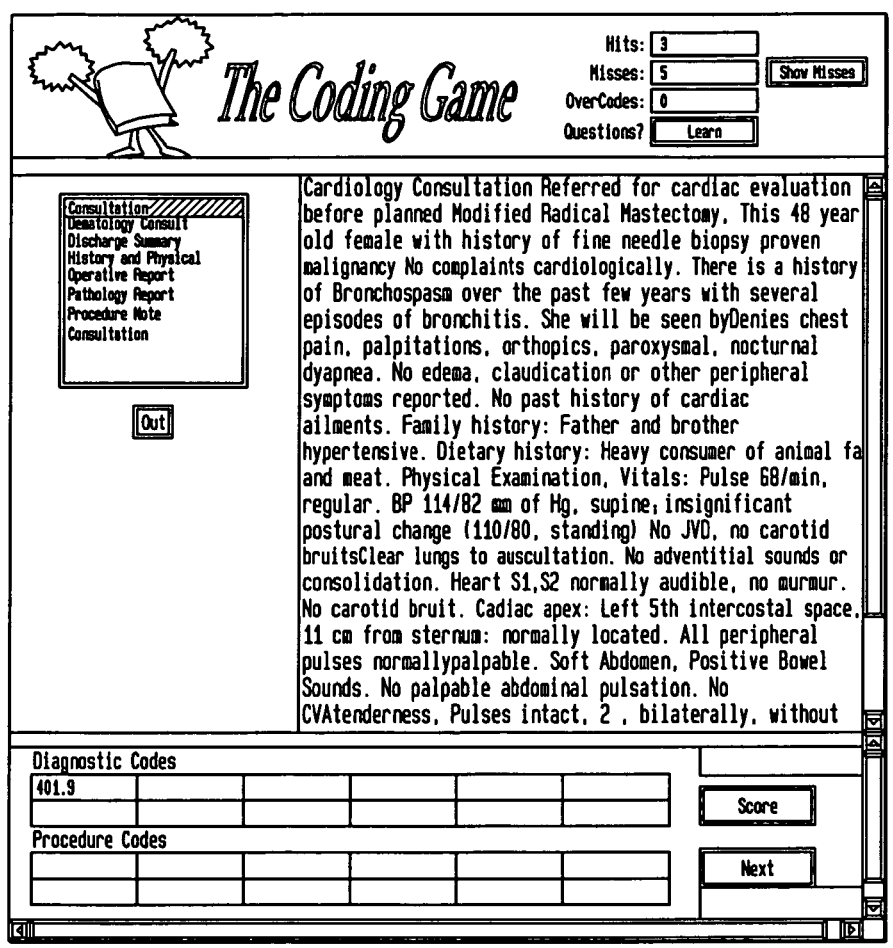
FIG. 4 shows an embodiment of a user interface display when assigning codes during a round one of a gaming embodiment of the present technology.
Figure 5:
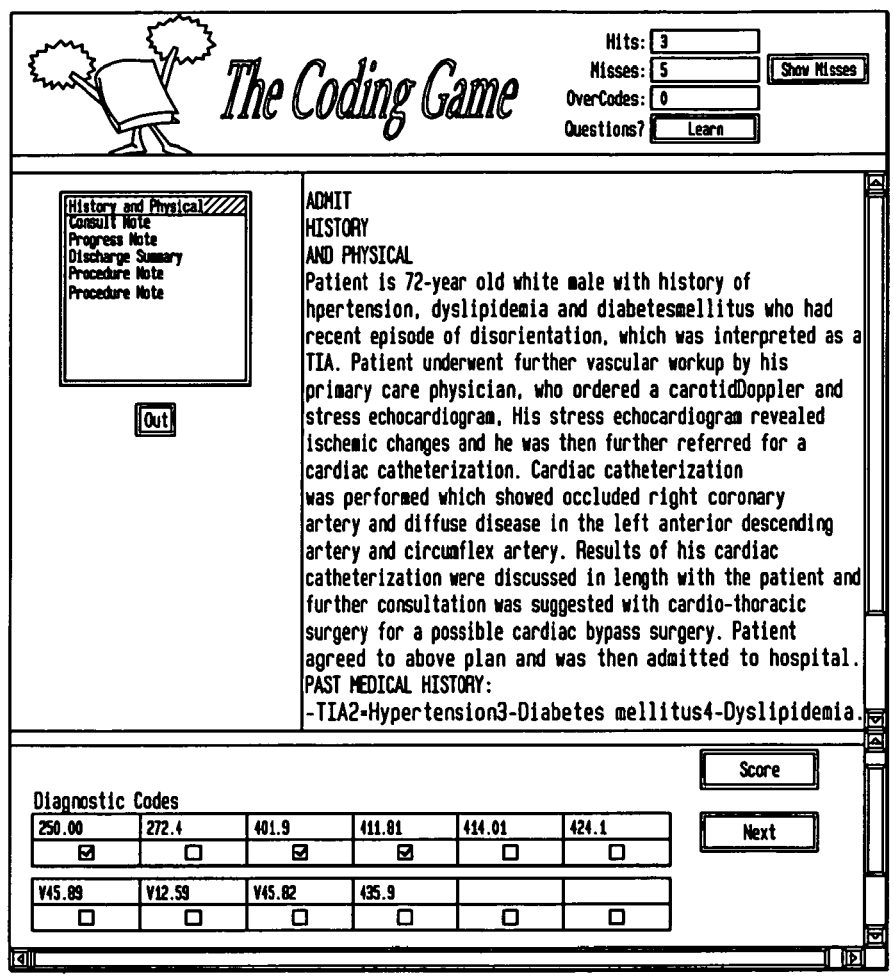
FIG. 5 shows an embodiment of a user interface display when voting on codes during a round two of a gaming embodiment of the present technology.

A game consisting of a series of cases is played by a group of coders, all of whom are asked to assign medical codes to the same collection of cases. Each case may consist of a series of component documents comprising a medical record or may be independent medical documents. Any established medical coding system can be used when playing this game (e.g. ICD-9, ICD-10, CPT, SNOMED, etc.). During each case, participants are exposed to a complete medical record or a single medical document (e.g. a History and Physical). Participants then respond in one of two ways:
1. For CCRs or URs, they assign one or more medical codes to the document or medical record. Assignments may be done through a web-based user interface as shown in FIG. 2, which shows an embodiment of a user interface display when assigning codes. Similarly, FIG. 4 shows another embodiment of a user interface display when assigning codes during a round one of the game embodiment.
2. For ICRs, they vote on whether one or more medical codes should be assigned to a medical record or document. When voting, participants respond "yes" or "no" for each of the nonconsensus codes presented. Voting occurs for each code assigned to a medical record or document. Voting may also occur through a web based user interface as shown in FIG. 3, which shows an embodiment of a generic user interface display when voting. Similarly, FIG. 5 shows another embodiment of a user interface display when voting on codes during a round two of a game embodiment.

Presenting participants with a mix of cases, some associated with consensus codes, some with incomplete or nonconsensus codes serves two needs of the game:
1. Keeping participants engaged by presenting them with immediate feedback on their submissions.
2. Expanding the body of medical records associated with consensus codes, CCRs.

The ratio of cases using CCRs to non-CCRs (URs and ICRs) is not fixed but is determined by the number of participants in the game. However, the number of CCR cases should be greater than the number of non-CCR cases to maintain participant interest.

Scoring

Participants receive a score based on their correct responses. A score is provided immediately during cases in which participants are coding records classified as CCRs. A score is provided after some delay when participants are coding or voting on records classified as either URs or ICRs. The length of the delay in scoring a UR or ICR cases is dependent on the amount of time it takes a criterion percentage of coders to agree on a set of codes to be associated with document or medical record used in the case and is wholly determined by the number of participants and the frequency with which they play the game. If the criterion percentage of coders is 80%, then when 80% of the coders have agreed with the codes assigned to a medical record or document used in a UR or ICR case, all participants who have coded these documents will receive positive or negative feedback depending on whether they assigned the consensus code. Under conditions in which many individuals are playing the game at the same time, feedback could be almost immediate. With lighter traffic the delay will be greater and some results might first become available the next time the coder player logs onto the site increasing the desire to repeatedly participate in the game.

Scoring will be based on two standard industry metrics, precision and recall. Both measures rely on the existence of something that represents "truth", in this case, the consensus codes associated with the medical record or document. A coder can either:
- Assign a code, when the code is also a consensus code (this is called a true positive or tp).
- Not assign a code, when the code is not a consensus code (this is called a true negative or tn).
- Not assign a code when the code is a consensus code (this is called a false negative or fn).
- Assign a code when the code is not part a consensus code (this is called a false positive or fp).

These four possibilities are summarized in the following table A-1 (after Manning & Schutze, 1999).

| A-1 | Consensual Code | |
| --- | --- | --- |
| Coder (Human) | Code Assigned | Code Not Assigned |
| Code Assigned | tp | fp |
| Code Not Assigned | fn | tn |

Precision is then defined as:

$$\text{precision} = \frac{tp}{tp + fp}$$

and recall is defined as:

$$\text{recall} = \frac{tp}{tp + fn}$$

The precision of a participant is simply the percentage of the items coded that were also consensus codes. The recall of the participant is the percentage consensus codes that the participant also coded.

The two measures can be combined into a measure called the F Measure (Manning & Schutze, 1999) which is defined as $$F = \frac{1}{\alpha(1/P) + (1-\alpha)1/R}$$

where P is precision, R is recall and α is a weight that determines the relative importance of precision and recall (typically this is set to 0.5). F statistics normally range from 0 to 1. To present a score that is easier to read, the F statistic will be multiplied by 100 when presented to a user.

Game Rounds

Individual games are structured into rounds.
Level 1: consists of participants who are new to the game or who have not had one of the top P scores in previous level 1 rounds (where P is a percentage assigned by the implementers of the game).

Level 2: consists of participants who obtained one of the P top scores in the most recent level one game played.

Level 3: consists of participants who had one of the P top scores in the most recent level 2 game played.

Additional rounds will be patterned like this with the Nth level round consisting of participants who had one of the P top scores in the most recent N−1 level played. This embodiment of the Coding Game does not have a fixed number of rounds. The number of rounds is wholly determined by the number of participants registered for the game.

Rankings

Participants playing the Coding Game will receive an overall score that reflects their performance within individual rounds and the round level that they have achieved. This overall score is determined by the following formula:

$$Score = 10 \Sigma \mu_{x/n}$$

Where $\mu_x$ is the average score a participant receives in a given round, n is the number of rounds, and x ranges from 1 to the number of rounds. This overall score will range from 0 to 1000. It reflects both the performance within each round as well as the level of round achieved. In a game with ten levels, individuals who have reached level four can have an overall score as high as 400. Those who have reached level 7 can have an overall score as high as 700, etc. Rankings will be determined by ordering scores highest to lowest.

Coding Game Products

The coding game yields several products that are of general use to the medical community. Specifically:

1. The Coding Game produces a corpus of medical records with associated medical codes that can serve as a gold standard for medical coding. The codes are the product of a process that drives participants towards consensus. Unlike other methods that might produce a gold standard, the Coding Game produces empirical data that justifies the assignment of each code. The consensus percentage represents a precise measure of the degree of agreement within the coding community that any particular code should be associated with any particular document.
    a. The gold standard itself has numerous uses including the screening of potential job applicants at medical institutions that do coding,
    b. the training of individuals for coding positions,
    c. the evaluation of various computer assisted coding software systems.
2. The Coding Game provides a precise measure of a human coder's ability. The scoring system that is part of the Coding Game can be used as a measure of this ability. The scale which ranges from 0 to 1000 is a much more precise metric than the current system that relies on inexact correlates to coding ability such as years of experience and passing a certification program.
    a. This metric is useful both to hiring institutions such as hospitals as well as to the coding community itself.
    b. The metric will provide greater transparency in the market place for medical coders allowing the best coders to command a premium for their services while institutions that hire medical coders can make intelligent tradeoffs between compensation and ability.
3. The Coding Game is a vehicle for training coders. Because it has been constructed to be enjoyable, coders will have an incentive to participate in the game. Through their participation, they will gain valuable experience and feedback on their coding ability. Like many pedagogic systems that provide experience and feedback, training is a natural consequence of this process.

Using the Delphi Method in a Game Setting for Other Content Domains

The methods and scoring algorithms described in this patent application are not restricted to Medical Coding. They can be applied to any domain that has the following characteristics:

1. There is significant variance (disagreement) among identified experts in the domain when asked to solve domain specific problems. Medical coders have a well documented history of variability of response when asked to code the same documents. However, the field of medical coding is not unique in this regard. A few examples from other domains include: medical diagnoses, legal precedent analysis and opinion, tax and accounting practices and property appraisal.
2. The potential responses that experts can provide are limited and objectively describable a priori. Like medical codes, the expert responses of an eligible domain for this kind of treatment must be easily described. For example a physician, rendering an opinion about a medical diagnosis is easily describable because medical diagnoses are limited and are well documented. An opinion rendered by an accountant about the legitimacy of writing off a particular deduction also falls into this category.

The above described embodiments may be programmed as software for computerized systems, such as PDA's, portable computers, desktop computers, networked computers or devices that can interact with servers and/or other networked devices over a network such as the Internet. For example in one embodiment, a method for coding medical documents using a digital processor may include presenting a set of documents to each of a plurality of game contestants in a user interface; receiving input from at least one of the user interfaces concerning a potential classification code for the set of documents; and determining a score for at least one of the plurality of game contestants based on the received input from the user interface. This method as previously described may further include determining an accepted classification code for the set of documents from input of the user interfaces of the plurality of game contestants. Moreover, this method as previously described may further include determining the score based on the determination of the accepted classification code.

Although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

APPENDIX 1

An Explanation of Sensitivity and Recall Measures

A computerized system as discussed previously may be implemented to measure or determine the accuracy of Coders and Computer Assisted Coding (CAC) with two standard industry metrics, precision and recall. Both measures rely on the existence of entity which represents truth, in this case, the consensual coding (gold) standard that is the product of the DMMC process. A coder, viewing the same set of medical records that are part of the gold standard either can:

Assign a code, when the code is also part of the consensual view (this is called a true positive or tp).

Not assign a code, when the code is not part of the consensual view (this is called a true negative or tn).

Not assign a code when the code is part of the consensual view (this is called a false negative or fn).

Assign a code when the code is not part of the consensual view (this is called a false positive or fp).

These four possibilities are summarized in table A-1 (after Manning & Schutze, 1999).

|  | Consensual View (Gold Standard) | |
| --- | --- | --- |
| Coder (machine or Human) | Code Assigned | Code Not Assigned |
| Code Assigned | tp | fp |
| Code Not Assigned | fn | tn |

Precision is then defined as:

$$precision = \frac{tp}{tp + fp}$$

and recall is defined as:

$$recall = \frac{tp}{tp + fn}$$

The precision of a coding system is simply the percentage of the items coded that were also part of the gold standard, the consensual view. The recall of the system is the percentage of gold standard items that the coding system also coded.

The two measures can be combined into a measure called the F Measure (Manning & Schutze, 1999) which is defined as:

$$F = \frac{1}{\alpha \frac{1}{p} + (1-\alpha)\frac{1}{R}}$$

where P is precision, R is recall and α is a weight that determines the relative importance of precision and recall (typically this is set to 0.5).

The invention claimed is:

1. A method for confirming accuracy of coders comprising:
establishing a collection of medical documents as a test sample;
determining, with a processor, a convergence of assigned medical codes for the test sample that have been assigned by a plurality of coders to establish a standard of one or more accepted medical codes for the test sample, wherein determining the convergence comprises:
comparing, with the processor, each medical code assigned by the plurality of coders to other assigned medical codes;
calculating an agreement amongst a number of coders from the plurality of coders for a given medical code assigned to the test sample, wherein the number of coders in agreement meets a certain percentage of the plurality of coders;
applying the test sample to a coding system to obtain one or more determined medical codes for the test sample; and
deriving with the processor a rate of accuracy of the coding system based on a correspondence between the determined codes and the accepted medical codes.

2. The method of claim 1 wherein the determined medical codes are obtained by a software coding algorithm that automatically assigns medical codes to the collection of medical documents.

3. The method of claim 1 wherein the deriving is performed by a software algorithm that automatically calculates a rate of the coding system.

4. The method of claim 1 wherein the plurality of coders includes at least one automated coding system.

5. The method of claim 1 wherein the determined medical codes are obtained by a computer system that assigns medical codes to the collection medical documents with a user interface of the computer system.

6. The method of claim 1 wherein the plurality of coders includes at least one automated coding system that accepts data medical codes assigned with a user interface of the coding system.

7. The method of claim 1 wherein the plurality of coders includes at least one automated coding system that includes a software algorithm that automatically assigns medical codes to the collection of medical documents.

8. An automated system for confirming accuracy of coders comprising:
a processor; and
a memory accessible by the processor, the memory storing instructions executable by the processor, comprising:
processor control instructions to establish a collection of electronic medical documents as a test sample;
processor control instructions to determine in a computer processor a convergence of assigned medical codes for the test sample that have been assigned by a plurality of coders to establish a standard of one or more accepted medical codes for the test sample, wherein processor control instructions determine the convergence by: comparing, with the processor, each medical code assigned by the plurality of coders to other assigned medical codes and calculating an agreement amongst a number of coders from the plurality of coders for a given medical code assigned to the test sample, wherein the number of coders in agreement meets a certain percentage of the plurality of coders;
processor control instructions to apply the test sample to a coding system to obtain one or more determined medical codes for the test sample; and
processor control instructions to derive with the computer processor a rate of accuracy of the coding system based on a correspondence between the determined codes and the accepted medical codes.

9. The automated system of claim 8 wherein the determined medical codes are obtained by a software coding algorithm that automatically assigns medical codes to the collection of medical documents.

10. The automated system of claim 8 wherein the deriving is performed by a software algorithm that automatically calculates a rate of the coding system.

11. The automated system of claim 8 wherein the plurality of coders includes at least one automated coding system.

12. The automated system of claim 8 wherein the determined medical codes are obtained by a computer system that assigns medical codes to the collection of medical documents with a user interface of the computer system.

13. The automated system of claim 8 wherein the plurality of coders includes at least one automated coding system that accepts data medical codes assigned with a user interface of the coding system.

14. The automated system of claim 8 wherein the plurality of coders includes at least one automated coding system that includes a software algorithm that automatically assigns medical codes to the collection of medical documents.

* * * * *